(12) United States Patent
Jonckers et al.

(10) Patent No.: US 6,921,838 B2
(45) Date of Patent: Jul. 26, 2005

(54) PROCESS FOR THE PREPARATION OF UREA

(75) Inventors: Kees Jonckers, Susteren (NL); Jozef Hubert Meessen, Gulpen (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/490,617

(22) PCT Filed: Sep. 26, 2002

(86) PCT No.: PCT/NL02/00626

§ 371 (c)(1),
(2), (4) Date: Sep. 8, 2004

(87) PCT Pub. No.: WO03/029196

PCT Pub. Date: Apr. 10, 2003

(65) Prior Publication Data

US 2005/0038293 A1 Feb. 17, 2005

(30) Foreign Application Priority Data

Oct. 1, 2001 (NL) .............................................. 1019081

(51) Int. Cl.⁷ ........................... C07C 273/04; B01J 8/04
(52) U.S. Cl. ........................ 564/70; 422/138; 422/189; 422/198; 422/202; 564/67; 564/68; 564/71; 564/72
(58) Field of Search .............................. 564/67, 68, 70, 564/71, 72; 422/188, 189, 198, 202

(56) References Cited

U.S. PATENT DOCUMENTS

| | | | | |
|---|---|---|---|---|
| 5,792,889 A | * | 8/1998 | Pagani | .......................... 564/67 |
| 6,284,922 B1 | | 9/2001 | Pagani | .......................... 564/72 |
| 2001/0031893 A1 | | 10/2001 | Pagani | .......................... 564/67 |

FOREIGN PATENT DOCUMENTS

| | | |
|---|---|---|
| EP | 155 735 | 9/1985 |
| EP | 1036787 | 9/2000 |

\* cited by examiner

*Primary Examiner*—Peter O'Sullivan
(74) *Attorney, Agent, or Firm*—Mayer Brown Rowe & Maw LLP

(57) ABSTRACT

The invention relates to a process for the preparation of urea from ammonia and carbon dioxide with the application of a synthesis reactor, a condenser, a scrubber and a stripper, wherein an outlet of the stripper, through which a gas stream is discharged during operation, is functionally connected to the inlet of the condenser and to the inlet of the reactor and wherein an outlet of the condenser is functionally connected to an inlet of the scrubber and wherein the obtained reaction mixture is stripped in the stripper in countercurrent with one of the starting materials, wherein the division of the gas stream from the stripper to the condenser and the reactor is completely or partly controlled by one or more controlling elements present in the non-common part of the functional connection between the outlet of the stripper and the inlet of the condenser and/or the inlet of the reactor.

13 Claims, 2 Drawing Sheets

PROCESS FOR THE PREPARATION OF UREA

CROSS REFERENCE TO RELATED APPLICATION

This application is the National Phase of International Application PCT/NL02/00626 filed Sep. 26, 2002 which designated the U.S., and that International Application was published under PCT Article 21(2) in English.

The invention relates to a process for the preparation of urea from ammonia and carbon dioxide, which preparation takes places wholly or partly with the application of a synthesis reactor (hereafter also briefly referred to as "reactor"), a condenser, a washing stage or "scrubber" and a decomposition stage or "stripper", with an outlet of the stripper, through which during operation a gas mixture is discharged, being functionally connected to the inlet of the condenser and to the inlet of the reactor and with an outlet of the condenser being functionally connected to an inlet of the scrubber and with the obtained reaction mixture being stripped in countercurrent with one of the starting materials.

In a process based on the stripping principle, urea may be prepared by introducing excess ammonia along with carbon dioxide into a synthesis reactor (hereafter briefly referred to as "reactor") or synthesis zone at a suitable pressure (for example 12–40 MPa) and a suitable temperature (for example 160–250° C.), which first results in the formation of ammonium carbamate according to the reaction:

2NH$_3$+CO$_2$→H$_2$N—CO—ONH$_4$

Dehydration of the ammonium carbamate formed then results in the formation of urea according to the equilibrium reaction:

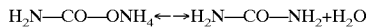
H$_2$N—CO—ONH$_4$←→H$_2$N—CO—NH$_2$+H$_2$O

The theoretically attainable conversion of ammonia and carbon dioxide into urea is determined by the thermodynamic position of the equilibrium and depends on for example the NH$_3$/CO$_2$ ratio (N/C ratio), the H$_2$O/CO$_2$ ratio and temperature.

In the conversion of ammonia and carbon dioxide to urea in the synthesis zone, a reaction product is obtained from the synthesis reactor which product is a urea synthesis solution which consists essentially of urea, water, ammonium carbamate and unbound ammonia.

Besides a urea synthesis solution, there may evolve in the synthesis reactor a gas mixture of unconverted ammonia and carbon dioxide along with inert gases, which gas mixture is also known as synthesis gas. The inert gases present herein may originate from for example a system that adds air to the plant in order to improve the plant's corrosion resistance. For example, inert gaseous components may be supplied to the synthesis reactor via the raw materials (NH$_3$ and CO$_2$). Ammonia and carbon dioxide are removed from the synthesis gas and are preferably returned to the synthesis reactor.

The synthesis reactor may comprise separate zones for the formation of ammonium carbamate and urea. These zones may, however, also be united in a single apparatus. The synthesis may be effected in a single reactor or in two reactors. If two reactors are employed, the first reactor, for example, may be operated with virtually fresh raw materials and the second with raw materials that are completely or partly recirculated from for example the urea recovery section.

The conversion of ammonium carbamate into urea and water in the synthesis reactor may be effected by ensuring a sufficiently long residence time for the reaction mixture in the reactor. The residence time will in general be longer than 10 min, preferably longer than 20 min. The residence time will in general be shorter than 3 hours, preferably shorter than 1 hour.

A urea plant operating on the stripping principle is understood to be a urea plant in which the decomposition of the ammonium carbamate that is not converted into urea and the expulsion of the customary excess ammonia largely take place at a pressure that is essentially virtually equal to the pressure in the synthesis reactor. This decomposition/expulsion takes place in a stripper downstream of the synthesis reactor with addition of heat and with or without addition of a stripping gas. In a stripping process, carbon dioxide and/or ammonia may be used as stripping gas before these components are added to the synthesis reactor. It is also possible to use thermal stripping here, which means that ammonium carbamate is decomposed exclusively by supplying heat and the ammonia and carbon dioxide present are removed from the urea solution. Stripping may be effected in two or more steps. In a known process a first, purely thermal stripping step is followed by a CO$_2$ stripping step with further addition of heat. The ammonia and carbon dioxide-containing gas stream exiting from the stripper is returned to the reactor whether or not via a condenser.

In a urea stripping plant the synthesis reactor is operated at a temperature of 160–240° C., preferably at a temperature of 170–220° C. The pressure in the synthesis reactor is 12–21 MPa, preferably 12.5–19.5 MPa. The N/C ratio in the synthesis reactor in a urea stripping plant is between 2.5 and 4.

A frequently used embodiment for the preparation of urea by a stripping process is the Stamicarbon® CO$_2$ stripping process as described in *Uhlmann's Encyclopedia of Industrial Chemistry*, Vol. A 27, 1996, pages 344–346.

After the stripping operation, the pressure of the stripped urea synthesis solution is reduced to a low level in the urea recovery section and the solution is concentrated by evaporation, after which urea is released and a low-pressure ammonium carbamate stream is recirculated to the synthesis reactor. Depending on the process, this ammonium carbamate may be recovered in either a single or a plurality of process steps operating at different pressures.

The larger part of the gas mixture obtained in the stripping treatment is condensed and adsorbed together with the ammonia needed for the process in a condenser, following which the resulting ammonium carbamate is transferred to the synthesis reactor for the formation of urea. In a standard Stamicarbon® CO$_2$ stripping plant the carbamate condenser operating at high pressure is usually designed as a so-called "falling-film" condenser. Here, the liquid flows down the inside surface of the tubes of this heat exchanger as a film, with the stripping gas flowing past it in countercurrent.

An improved design of the carbamate condenser is the so-called "submerged condenser" as described in NL-A-8400839. In comparison with the conventional falling film condenser, this type of condenser has the advantage that the liquid as a rule has a longer residence time, resulting in extra urea formation in the condensor, which increases the total plant production capacity without any substantial investment. The submerged condenser, in horizontal form also known as "pool condenser", may be placed horizontally or vertically.

EP-A-1036787 describes a process for modernizing a urea plant wherein the existing falling-film condenser is transformed into a submerged condenser. To that end, an overflow weir is installed for the liquid phase in such a way that the condenser is filled with liquid when the plant is in operation. The liquid is passed to the synthesis reactor via a weir. By introducing the gas stream from the stripper in the bottom of the condenser and having the discharge take place via the top, the whole operates as a submerged condenser. The main advantage of such a process is improved heat transfer in the process. Consequently, the urea reaction may start spontaneously, permitting either another temperature increase (by about 170° C. to 183° C. because of the composition) or a higher steam pressure or a higher plant load. A combination of these advantages may also be achieved.

A known drawback of the use of a submerged condenser is that the pressure drop across the condenser that is caused by the process is greater than when a falling-film condenser is used. The gas mixture undergoing submerged condensation will undergo a pressure drop at least equal to the height of the liquid column through which the gas bubbles. This usually means a pressure drop of 10–15 metres' liquid column. However, the driving force in the synthesis loop of an existing plant, that is, the loop that connects the high-pressure equipment and is formed by the combination of stripper-condenser-reactor-stripper, is only 8–10 metres' liquid column. Since the pressure drop of the gas in the condenser is greater than the driving force in the synthesis loop, the gas phase exiting from the condenser can no longer take part in this main circulation.

In EP-A-1036787 this problem is resolved by passing the gas from the condenser to a high-pressure scrubber. In the high-pressure scrubber the condensable components that are passed from the condenser to the high-pressure scrubber are absorbed in the carbamate stream coming from the urea recovery section. The non-condensed inert gases are discharged to the atmosphere here. This means, however, that the gas from the condenser is not returned to the synthesis reactor and that air/oxygen is not therefore supplied to the reactor as a corrosion inhibitor. Accordingly, EP-A-1036787 suggests passing a portion of the gas stream coming from the stripper to the reactor and the remainder to the condenser.

Controlling the process to obtain a proper division of the gas stream coming from the stripper is a critical affair, however. When too little gas from the stripper is supplied to the synthesis reactor, the exothermic carbamate formation supplies insufficient heat to maintain the reactor temperature. The temperature in the reactor will thereby decrease to too low a level. This has a dramatic negative effect on the kinetics of the carbamate dehydration, resulting in too low a conversion in the urea synthesis. This leads to too high a load of the stripper and the condenser. Furthermore, insufficient supply of gas from the stripper to the synthesis reactor involves a considerable risk of insufficient oxygen being supplied to the reactor, with the risk of corrosion in the reactor.

If too much gas from the stripper is supplied to the synthesis reactor, the gas stream from the reactor to the high-pressure scrubber will increase, and this may lead to overloading of the scrubber, which will rapidly result in an increase in the reactor pressure to an undesirably high level, which is undesirable from a safety point of view. Additionally, too large a supply of gas from the stripper to the synthesis reactor is attended by a reduced gas supply to the condenser, because of which less steam develops in the condensor. Consequently, too much gas to the reactor has a negative effect on the economy of the process.

In EP-A-1036787 the division of the gas stream from the stripper to the reactor and to the condenser is controlled with a single valve which is installed between the carbamate condenser and the high-pressure scrubber (see FIGS. 3 and 5; control valve 45). This solution of the division problem has a few important drawbacks:

1°. In order to keep the liquid level in the condenser below the overflow weir, the pressure drop across this control valve will in general need to be between 0.1 and 0.3 MPa. This is because, without a pressure drop across this control valve, the carbamate condenser and the reactor would form communicating vessels, with the level in both vessels tending to be at the same height. In other words, without this control valve the liquid level in the condenser will rise up and into the conduit connecting the condenser to the scrubber, i.e. up to a height virtually corresponding to the height of the liquid level in the reactor. It will be clear, then, that a pressure drop needs to be created across this control valve corresponding to the liquid height between the liquid level in the reactor on the one hand and the desired liquid level in the condenser on the other. Given the differences in height in commercial plants for the preparation of urea, this pressure drop amounts to 0.1–0.3 MPa ($\cong$10–30- metres liquid column). The pressure drop between the stripper and the reactor and between the stripper and the condenser due to friction in the conduits is very low in comparison with the pressure drop across the aforementioned control valve in the conduit between the condenser and the high-pressure scrubber. In practice this implies that control of the division of the stripping gas by means of this single control valve will result in on/off switching; the gas stream from the stripper will then either flow entirely to the reactor or entirely to the condenser. This will result in an unstable process with a highly negative effect on safety, economy and production aspects of the plant.

2°. The position of, and the pressure drop across, the aforementioned control valve affects the liquid level in the overflow compartment at the back of the overflow weir of the described condenser (see FIGS. 3 and 4; plate 41).

It should be realized that the overflowing liquid forms part of the main loop of the recirculation system of the urea synthesis: reactor-stripper-condenser-reactor. The flow in this circulation loop is entirely based on the force of gravity. Thus, the liquid level in the overflow compartment influences the available gravity driving force in this loop: when the liquid level drops, the available pressure drop in this synthesis circulation loop will decrease. Taking into account the process dynamic behaviour, variations in the position of the control valve will lead to chaotic flow behaviour in the synthesis circulation loop, with all serious negative consequences for safety, the economy and the production aspects of the plant.

The object of the present invention is to provide an improved process and plant for the preparation of urea wherein the aforementioned division problem of the gas stream from the stripper to the reactor and/or from the stripper to the condenser is completely eliminated or eliminated to a considerable extent.

According to the invention it has now surprisingly been found that the aforementioned problem can effectively be resolved by completely or partly controlling the division of the gas stream from the stripper to the condenser and the reactor with the aid of one or more controlling elements that are located in the non-common part of the functional connection between the outlet of the stripper and the inlet of the condenser and/or the inlet of the reactor.

In a first embodiment of the invention a controlling element is provided in the non-common part of the functional connection between the outlet of the stripper and the inlet of the condenser.

In a second embodiment of the invention a controlling element is provided in the non-common part of the functional connection between the outlet of the stripper and the inlet of the reactor.

In a third embodiment of the invention, which is preferred, a controlling element is provided in both the non-common part of the functional connection between the outlet of the stripper and the inlet of the condenser and between the outlet of the stripper and the inlet of the reactor. In this manner, the gas streams from the stripper to the condenser and the reactor can be controlled most accurately, depending on the further process conditions that are known to one skilled in the art or can be determined and tuned to each other on a routine basis by one skilled in the art.

One skilled in the art also has at their disposal an arsenal of controlling elements that may be used in the present invention. Suitable controlling elements include control valves (also known as regulating valves), shut-off valves and limited or calibrated restriction orifices in the functional connecting conduits. Pumps and/or compressors may also be used at suitable locations in the conduits so as to create such pressure differences that a desired division of the gas stream from the stripper to the condenser and/or the reactor is obtained. If a plurality of controlling elements are used, they may be of the same type but also may be of a different type. It is possible, for instance, to install in both the conduit from the stripper to the condenser and the conduit from the stripper to the reactor restriction orifices, each suitably sized, to ensure a pressure drop, and hence a division of the gas stream among the two conduits under all conditions. In place thereof it is also possible to install in the two aforementioned conduits adjustable pressure regulating valves that impart maximum flexibility to the embodiment of the process, in which case the investment costs will in principle be higher. It is also possible, for instance, to install a pressure regulating valve only in the conduit between the stripper and the reactor and a restriction orifice in the conduit between the stripper and the condenser, so that a compromise between operational flexibility and the investment costs is reached.

According to the invention, it is preferred for a submerged condenser operating as such to be used as a condenser. Such a condenser may be an original submerged condenser as described in NL-A-8400839, either a horizontal design or a vertical design, but also a falling-film condenser transformed into a submerged condenser as described in EP-A-1036787. If desired, a falling-film condenser may be used as such, but this design is not preferred.

It is noted that a controlling element may also be present in the functional connection between the outlet of the condenser and the inlet of the scrubber, as described in for example EP-A-1036787. This controlling element may be used together with the above defined controlling elements according to the invention so as to obtain accurate division of the gas streams between the stripper, the condenser respectively the reactor.

In a fourth embodiment of the invention, the reactor, the condenser and the functional connection between the outlet of the condenser and the inlet of the scrubber are so designed that the reactor and the condenser function as two communicating vessels with the liquid level in the reactor respectively the condenser and in the outlet at the top of the condenser being at the same level. This may be accomplished by removing the overflow weir (41) in the condenser described in EP-A-1036787 as well as the controlling element in the connection between the outlet of the condenser and the scrubber. It will be clear to one skilled in the art that minor level differences may occur in the system of communicating vessels thus formed as a result of density differences between the liquid and the gases and minor differences in the gas load.

The gases from the condenser will leave the condenser via the conduit to the scrubber, with gas/liquid separation taking place in this conduit at the location where the liquid level is established. This liquid level is largely determined by the height of the weir in the reactor. A gas/liquid separating device is preferably provided in the outlet of the condenser to the scrubber at or near the location where the liquid level is present. Any gas/liquid separating device is in principle suitable for this purpose. For cost considerations it may be useful to use a settler or a cyclone. Use may also be made of other separating devices that present specific advantages but in general result in higher investment costs.

It is of advantage for the gas stream, preferably when the condenser is a submerged condenser operating as such and the gas stream leaves this condenser through the top, to undergo an extra scrubbing step before this gas stream is passed to the high-pressure scrubber. This extra scrubbing step is described more closely in the simultaneously filed and conjunctive Dutch patent application No. 1019080, whose content is incorporated herein by reference.

The process described above in the various embodiments, which for that matter are not limiting and may readily be modified by one skilled in the art without departing from the principle of the invention, is also highly suitable for improving and optimising existing urea plants, whereby the described advantages will also become manifest.

Furthermore, the invention as described above may be practiced in both new and existing urea stripping processes. Examples of urea stripping processes wherein the invention may be practiced are the Stamicarbon® $CO_2$ Stripping process, the Ammonia Stripping process, the Self-Stripping process, the ACES process (Advanced process for Cost and Energy Saving) the IDR (Isobaric-Double Recycle) process and the HEC process.

Therefore, the invention relates to a process for improving and/or optimising a urea plant, which urea plant essentially comprises a synthesis reactor, a condenser, a scrubber and a stripper, wherein an outlet of the stripper, through which a gas mixture is discharged during operation, is functionally connected to an inlet of the condenser and with an inlet of the reactor, and wherein an outlet of the condenser is functionally connected to an inlet of the scrubber and wherein the obtained reaction mixture is stripped in the stripper in countercurrent with one of the starting materials, wherein the division of the gas stream from the stripper to the condenser and the reactor is completely or partly controlled by one or more controlling elements present in the non-common part of the functional connection between the outlet of the stripper and the inlet of the condenser and/or the inlet of the reactor. Preferred embodiments are essentially the same as described above in relation to the preparation of urea according to the invention.

The invention further relates to a urea plant comprising a high-pressure zone essentially consisting of a synthesis reactor, a condenser, a scrubber and a stripper, wherein an outlet of the stripper, through which a gas stream is discharged during operation, is functionally connected to an inlet of the condenser and to an inlet of the reactor, and wherein an outlet of the condenser is functionally connected to an inlet of the scrubber and wherein the obtained reaction mixture is stripped in the stripper in countercurrent with one of the starting materials, wherein one or more controlling elements are present in the non-common part of the functional connection between the outlet of the stripper and the inlet of the condenser and/or the inlet of the reactor essentially in order to control the division of the gas stream between the outlet of the stripper and the inlet of the condenser respectively the reactor. Preferred embodiments of the urea plant are essentially in line with the above described preferred embodiments relating to the preparation of urea according to the invention as well as the process for improving and/or optimising a urea plant.

The invention is elucidated with reference to the following example.

Figure 1:
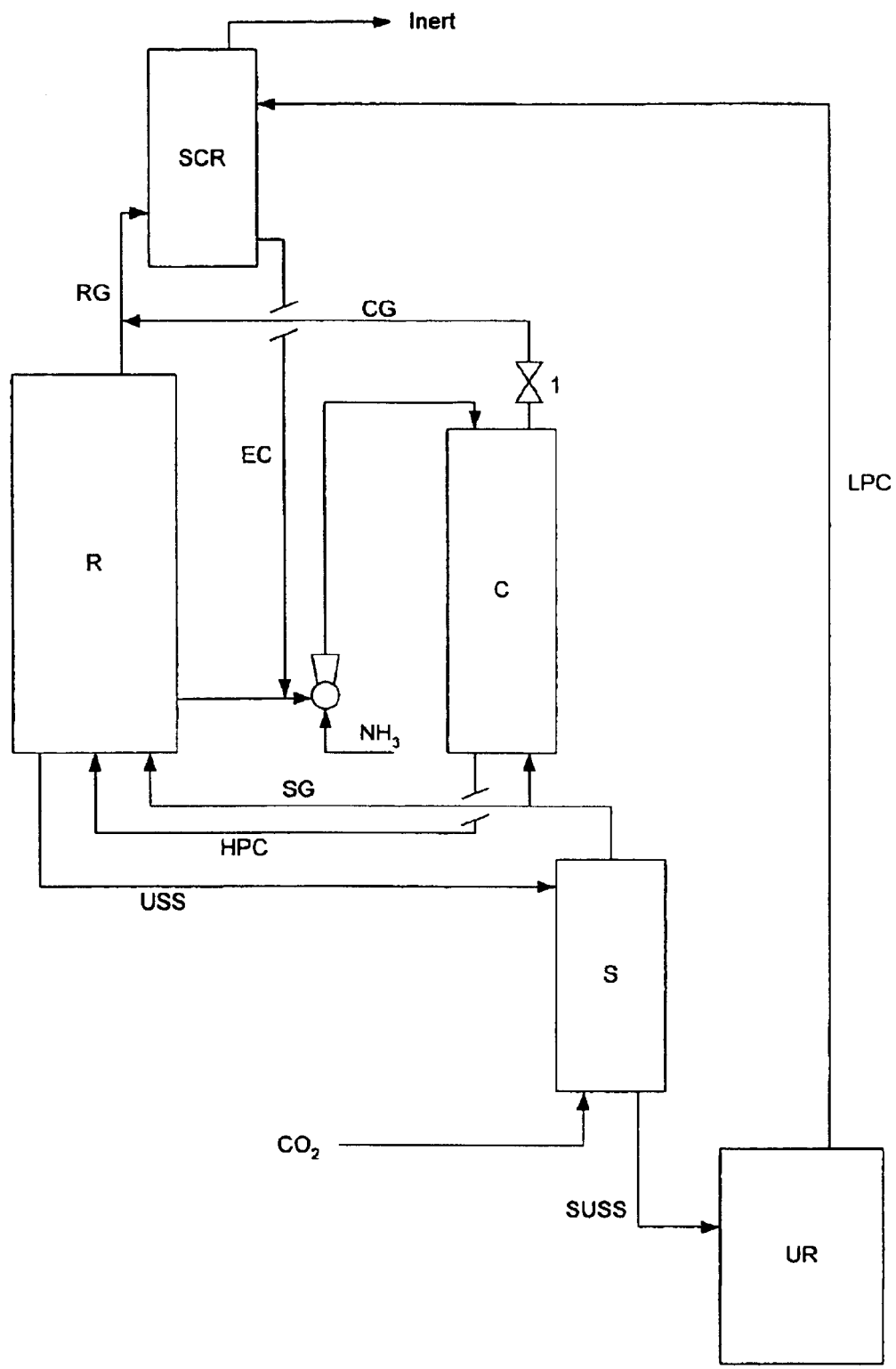
FIG. 1 is a schematic representation of a part of a urea plant according to the state of the art, for example as described in EP-A-1 036 787.

In FIG. 1, R represents a reactor essentially as described in EP-A-1 036 787, wherein carbon dioxide and ammonia are converted into urea.

The urea synthesis solution (USS) coming from the reactor is passed to a $CO_2$ stripper (S) wherein the USS is converted into a gas stream (SG) and a liquid stream (SUSS) by stripping the USS with $CO_2$. The gas stream (SG) coming from the $CO_2$ stripper consists essentially of ammonia and carbon dioxide, which is partly returned to the reactor (R) and partly to the condenser (C). The stream that contains the stripped urea synthesis solution SUSS is passed to the urea recovery (UR), where urea (U) is liberated and water (W) is discharged (U and W are not shown). In the UR there is obtained a low-pressure ammonium carbamate (LPC) stream, which is recycled to the high-pressure scrubber (SCR). In this (first) scrubber, the LPC is contacted with the gas stream (RG) coming from the reactor, which stream essentially consists of ammonia and carbon dioxide but additionally contains the inerts (non-condensable components) present in the carbon dioxide feedstock and ammonia feedstock. The enriched carbamate stream (EC) coming from the SCR is optionally combined with a stream that may come from the reactor and is passed, via an ammonia-driven ejector, to the high-pressure carbamate condenser (C) wherein the SG stream from the stripper is condensed with the aid of EC. The resulting high-pressure carbamate stream (HPC) is returned to the reactor and the gas stream (CG) coming from the condenser is supplied through a conduit provided with control valve 1 to the high-pressure scrubber (SCR), in this case combined with the gas stream from the reactor (RG). In this example, the fresh ammonia is supplied to the high-pressure carbamate condenser (C) via an ejector but may of course also be supplied elsewhere in the R→S→C→R loop or in the R→SCR→C→R loop.

Figure 2:
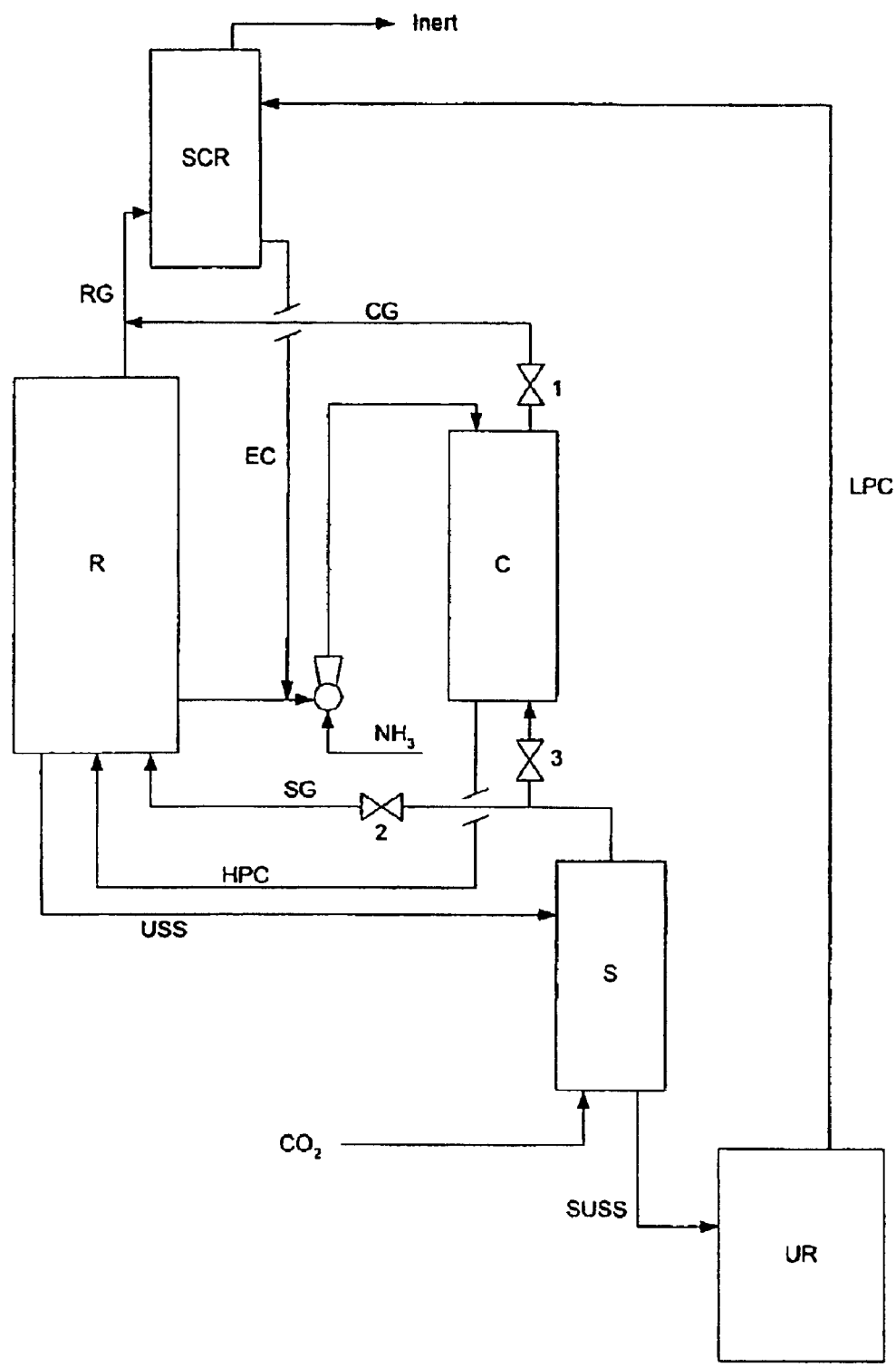
FIG. 2 is a schematic representation of a part of a urea plant according to the present invention.

FIG. 2 shows an improvement on the state of the art in accordance with the invention, wherein a control valve 2 is provided in the conduit from the stripper (S) to the reactor (R) and the condenser (C) in the non-common part to the reactor and a control valve 3 is provided in the non-common part to the condenser.

It will be clear that a number of variants and modifications of the present invention and the described embodiment are possible that are within the realm of one skilled in the art on the basis of this description and their expertise. Such variants are all within the scope of the present invention and are defined by the following claims.

What is claimed is:

1. Process for the preparation of urea from ammonia and carbon dioxide, which preparation takes places wholly or partly with the application of a synthesis reactor, a condenser, a scrubber and a stripper, wherein an outlet of the stripper, through which a gas stream is discharged during operation, is functionally connected to the inlet of the condenser and to the inlet of the reactor and wherein an outlet of the condenser is functionally connected to an inlet of the scrubber and wherein the obtained reaction mixture is stripped in the stripper in countercurrent with one of the starting materials, and wherein the division of the gas stream from the stripper to the condenser and the reactor is completely or partly controlled by one or more controlling elements present in the non-common part of the functional connection between the outlet of the stripper and the inlet of the condenser and/or the inlet of the reactor.

2. Process according to claim 1, wherein the division of the gas stream from the stripper to the condenser and the reactor is completely or partly controlled by a controlling element present in the non-common part of the functional connection between the outlet of the stripper and the inlet of the condenser.

3. Process according to claim 1, wherein the division of the gas stream from the stripper to the condenser and the reactor is completely or partly controlled by a controlling element present in the non-common part of the functional connection between the outlet of the stripper and the inlet of the reactor.

4. Process according to claim 1, wherein the division of the gas stream from the stripper to the condenser and the reactor is completely or partly controlled by two controlling elements, with the first controlling element being present in the non-common part of the functional connection between the outlet of the stripper and the inlet of the condenser and with the second controlling element being present in the non-common part of the functional connection between the outlet of the stripper and the inlet of the condenser.

5. Process according to claim 1, wherein the controlling element is chosen from the group consisting of control valves, shut-off valves, limited or calibrated restriction orifices, pumps and compressors.

6. Process according to claim 1, wherein the condenser is a submerged condenser operating as such, of horizontal or vertical design, or a falling-film condenser.

7. Process according to claim 1, wherein the reactor, the condenser and the functional connection between the outlet of the condenser and the inlet of the scrubber are so designed that the reactor and the condenser function as two communicating vessels, with the liquid level in the reactor and the condenser as well as in the outlet of the condenser being at the same level.

8. Process according to claim 7, wherein a gas/liquid separating device is provided in the outlet of the condenser to the scrubber at or near the location where the liquid level is present.

9. Process according to claim 1, wherein the condenser is a submerged condenser operating as such and the gas stream from the top of the submerged condenser is subjected to an extra washing step before this gas stream is passed to the scrubber.

10. Process for improving and/or optimising a urea plant, which plant essentially comprises a synthesis reactor, a condenser, a scrubber and a stripper, wherein an outlet of the stripper, through which a gas stream is discharged during operation, is functionally connected to the inlet of the condenser and to the inlet of the reactor and wherein an outlet of the condenser is functionally connected to an inlet of the scrubber and wherein the obtained reaction mixture is stripped in the stripper in countercurrent with one of the starting materials, and wherein the division of the gas stream from the stripper to the condenser and the reactor is completely or partly controlled by one or more controlling elements present in the non-common part of the functional connection between the outlet of the stripper and the inlet of the condenser and/or the inlet of the reactor.

11. Process for improving and/or optimising a urea plant according to claim 10, wherein the division of the gas stream from the stripper to the condenser and the reactor is completely or partly controlled by a controlling element present in the non-common cart of the functional connection between the outlet of the stripper and the inlet of the reactor.

12. Urea plant comprising a high-pressure section consisting essentially of a synthesis reactor, a condenser, a scrubber and a stripper, wherein an outlet of the stripper, through which a gas stream is discharged during operation, is functionally connected to the inlet of the condenser and to the inlet of the reactor and wherein an outlet of the condenser is functionally connected to an inlet of the scrubber and wherein the obtained reaction mixture is stripped in the stripper in countercurrent with one of the starting materials, characterized in that one or more controlling elements are provided in the non-common part of the functional connection between the outlet of the stripper and the inlet of the condenser and/or the inlet of the reactor essentially in order to control the division of the gas stream between the outlet of the stripper and the inlet of the condenser respectively the reactor.

13. Urea plant according to claim 12, wherein the division of the gas stream from the stripper to the condenser and the reactor is completely or partly controlled by a controlling element present in the non-common part of the functional connection between the outlet of the stripper and the inlet of the reactor.

* * * * *